United States Patent
Wilson

(10) Patent No.: US 7,351,264 B2
(45) Date of Patent: Apr. 1, 2008

(54) LINER FOR PROSTHESIS

(76) Inventor: Michael T. Wilson, 2711 Cartwright Rd., Missouri City, TX (US) 77459-2602

( * ) Notice: Subject to any disclaimer, the term of this patent is extended or adjusted under 35 U.S.C. 154(b) by 203 days.

(21) Appl. No.: 11/161,231

(22) Filed: Jul. 27, 2005

(65) Prior Publication Data

US 2007/0027556 A1    Feb. 1, 2007

(51) Int. Cl.
*A61F 2/80* (2006.01)
(52) U.S. Cl. .......................... 623/36; 602/63
(58) Field of Classification Search ............ 623/32–36; 602/62, 63, 77; 264/222
See application file for complete search history.

(56) References Cited

U.S. PATENT DOCUMENTS

| | | | |
|---|---|---|---|
| 4,822,371 A | 4/1989 | Jolly et al. | |
| 4,923,474 A | 5/1990 | Klasson et al. | |
| 5,314,497 A | 5/1994 | Fay et al. | |
| 5,376,129 A | 12/1994 | Faulkner et al. | |
| 5,376,132 A | 12/1994 | Caspers | |
| 5,507,834 A | 4/1996 | Laghi | |
| 5,658,354 A | 8/1997 | Norvell | |
| 5,888,216 A | 3/1999 | Haberman | |
| 6,059,834 A * | 5/2000 | Springs | 623/32 |
| 6,136,039 A | 10/2000 | Kristinsson et al. | |
| 6,508,842 B1 | 1/2003 | Caspers | |
| 6,793,682 B1 | 9/2004 | Mantelmacher | |
| 6,869,560 B1 | 3/2005 | Drouin et al. | |

* cited by examiner

*Primary Examiner*—Bruce Snow
(74) *Attorney, Agent, or Firm*—Conley Rose, P.C.

(57) ABSTRACT

A liner for use with a prosthesis comprises an inner layer, a cushion layer, an outer layer, and a bead defining the upper edge of the liner. The bead can be disposed between the inner and outer layers and may comprise an elastomeric material of non-uniform thickness. A method for making a prosthesis liner comprises a) making a positive of the residual limb, b) constructing an inner layer on the outer surface of the positive, c) defining an upper edge of the liner, d) forming a mold that reflects the shape of the positive and the defined upper edge, e) using the mold to shape a cushion layer that has a defined upper edge, f) applying a bead along the desired upper edge of the liner, g) applying the cushion layer to the inner layer; and h) constructing an outer layer on the outer surface of the cushion layer.

18 Claims, 2 Drawing Sheets

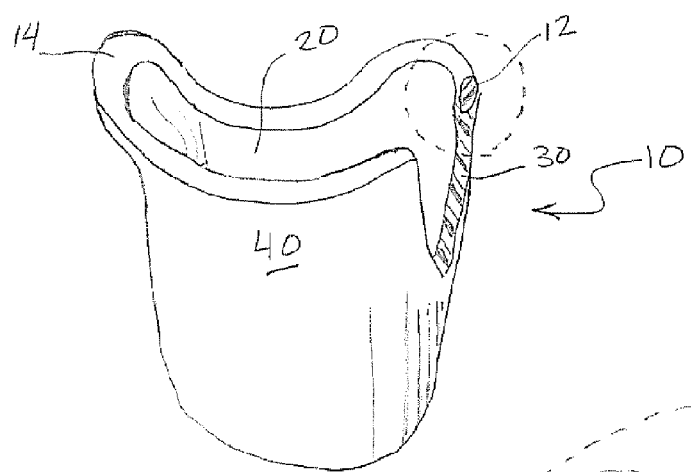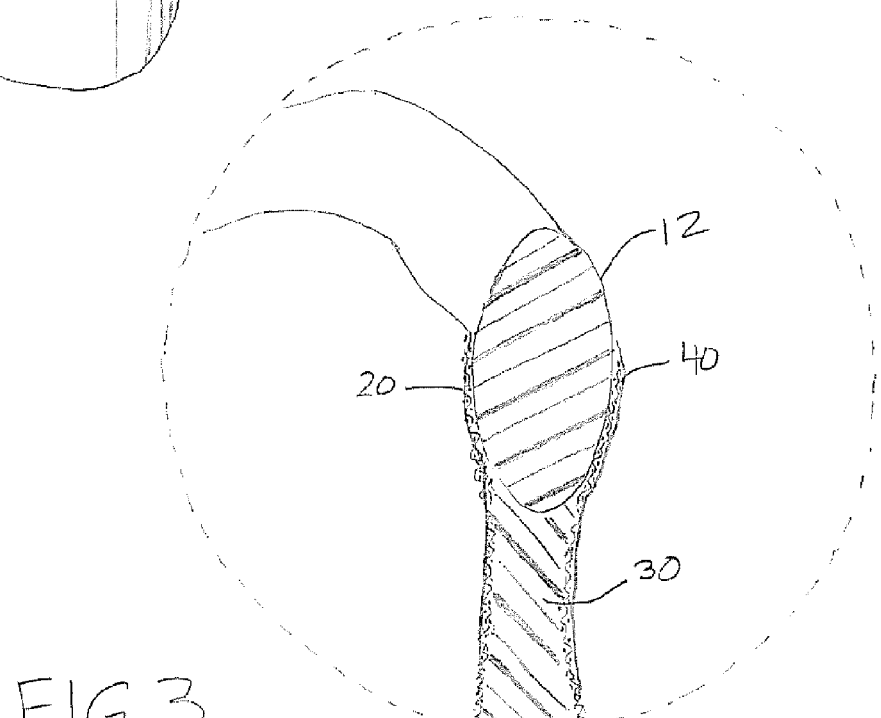

LINER FOR PROSTHESIS

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The present invention relates generally to liners for use with prosthetic devices and more particularly to a method for manufacturing liners having an improved proximal edge.

BACKGROUND OF THE INVENTION

Prosthesis suspension liners formed from silicone elastomeric materials have been described in prior patents, such as, for example, U.S. Pat. Nos. 4,923,474, 5,507,834, 5,376,129, 5,658,354, 5,888,216, 6,136,039, and 6,508,842. Elastomeric liners are commonly used to cushion a post-operative stump or residual limb with respect to a prosthesis. The prosthesis will typically include a rigid socket that is shaped to receive the stump or residual limb. The socket is installed over the residual limb and may be coupled to the liner by a locking element.

It is desirable that such liners conform to the outer surface of the residual limb and provide a comfortable cushion between the residual limb and the rigid socket of the prosthesis that is to be fitted over the residual limb. Special silicone rubber or elastomeric materials have been formulated as suitable substances for suspension liners. Such materials are typically selected on the basis of one or more of the following properties: hardness (or softness), elongation, tensile strength, sterilizability, porosity, and ease of cleaning. In particular, composite materials including silicone have been used successfully for suspension liners.

Despite advances in the materials, certain aspects of prosthesis liners remain sub-optimal. One such aspect is the upper or proximal edge of the liner. In instances where die prosthesis is held in place through mechanical engagement between the socket and the liner, the liner is in turn held in place by air pressure. With the limb in place within the liner, the gap between the edge of the liner and the limb is sealed to prevent the ingress of air into the space around the limb. This prevents air from entering the space between the limb and the liner For this reason, the term "suction socket" is occasionally used. The sealing method often requires applying pressure around the upper edge of the liner. However if the upper edge of the liner is not constructed with this consideration in mind, the contact and pressure of the liner edge on the limb can cause extreme discomfort.

Even in instances where a seal is not required, the liner may cause difficulty. For example, the liner may be too long, or may be finished or cut in such a manner that its upper edge causes the wearer discomfort. Hence, it remains highly desirable to provide the amputee with a optimal feeling of comfort at the residual limb interface with the prosthesis while maintaining strength and durability of the liner.

SUMMARY OF THE INVENTION

The present invention provides a prosthesis liner that includes an improved proximal edge having a rounded bead that is, in certain embodiments, shaped and configured to provide optimum comfort to the wearer. The present invention further includes a method for constructing liners having improved proximal edges. The method may include forming a pattern, flattening the pattern, defining an edge of the pattern, filling the pattern with a desired elastomer, forming the elastomer into the desired liner shape, and applying a desired bead material to the proximal edge of the liner. The steps and construction of the preferred liners are discussed in detail below.

Thus, the present invention comprises a combination of features and advantages that enable it to provide improved comfort and durability over previously known devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein:

FIG. 2 is a side view of a liner constructed in accordance with a first embodiment of the invention, showing one edge of the liner cut in order to show its cross-section; and FIG. 3 is an enlarged partial cross-section of the liner of FIG. 2.

DETAILED DESCRIPTION OF THE PREFERRED EMBODIMENT

Figure 1:
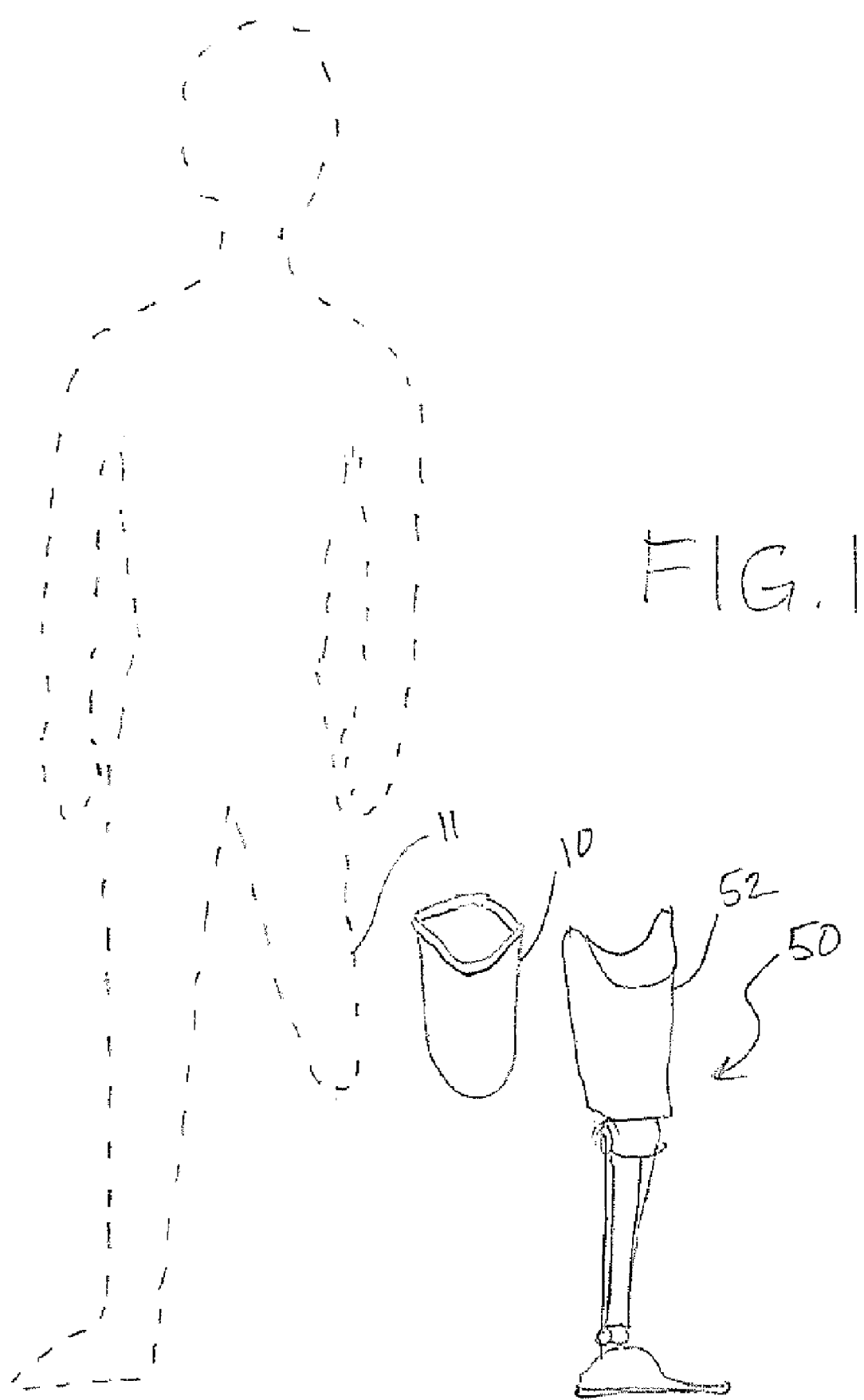
FIG. 1 is an illustration showing an amputee with liner and prosthetic limb doffed.

Referring initially to FIG. 1, an amputee who has had a limb partially removed will typically have a stump or "residual limb" 11, to which a prosthesis for the missing limb part can be attached. While FIG. 1 shows a transfemoral amputee and the discussion below may be presented in terms of a prosthetic leg, it will be understood that the present invention can be used advantageously in any partial limb amputation, including but limited to transfemoral and transtibial amputations. In FIG. 1, the liner 10 and the prosthesis 50 are shown separated from the wearer. Prosthesis 50 includes a socket 52, which is typically rigid and custom-shaped to conform generally to the outer surface of the partial limb 11.

As stated above, liner 10 fits over the partial limb and forms a cushion between the partial limb 11 and socket 52. Thus, liner 10 can have a great effect on the level of comfort experienced by the wearer. In particular, the configuration of the upper edge of liner 10 is important in ensuring wearer comfort.

Referring now to FIGS. 2 and 3, a preferred embodiment of the present liner 10 includes a inner layer 20, a cushion layer 30, and an outer layer 40. Inner layer 20 and outer layer 40 each preferably comprise at least one layer of elastomer-impregnated fiber, such as knitted nylon mesh or the like impregnated with polyurethane, silicone, or the like. Cushion layer 30 is preferably elastomeric and preferably comprises a relatively thick layer of silicone gel. Alternatively, cushion layer 30 may comprise urethane rubber, expanded closed cell EVA, closed cell silicone sponge, or any other suitable material.

Around the upper edge of liner 10 is a molded bead 12. In some embodiments, bead 12 is positioned at least partially between inner layer 20 and outer layer 40. In other embodiments (not shown), bead 12 is positioned inside inner layer 20 or outside outer layer 40. In still other embodiments, bead 12 may be disposed adjacent to the edges of inner and outer layers 20, 40.

Bead 12 preferably comprises a continuous or joined loop of elastomeric material, such as silicone or urethane. The thickness of bead 12 may be varied along the length of the loop, as illustrated at 14 in FIG. 2. The thickness of bead 12 can be designed to provide optimized comfort to the wearer. For example, it has been that wearer comfort can be enhanced when bead 12 is thicker at the portion of liner 10 that lies adjacent to the inner thigh of the wearer and thinner at the portion of liner 10 that lies adjacent to the outer thigh of the wearer. In some embodiments, bead 12 will range from 0.18 to 0.5 inch thick.

While any suitable method can be used to assemble a liner 10 in accordance with the present invention and having the desired traits of comfort and durability, a preferred method is as follows. First, a plaster cast of the wearer's stump or residual limb is taken and used to make plaster positive model. Next inner layer 20 is applied to the outside of the positive model. Inner layer 20 preferably comprises a laminated composite layer and may be formed by any suitable means. In one embodiment, one, two or more layers of stockinet comprising two-way stretch nylon, glass fiber or other suitable material are used for inner layer 20. This fiber layer is enclosed in an airtight film, which is then evacuated. The matrix portion of the composite inner layer, such as liquid silicone, is introduced to the stockinet layer and is forced by atmospheric pressure to flow into and impregnate the stockinet. Once the stockinet is fully impregnated, the airtight film is removed.

Bead 12 is applied to the desired configuration of the upper edge of the liner, preferably using silicone glue. A transfer layer such as tape or another transfer means is then applied over inner layer 20, the desired upper edge of the liner 10 is marked on the transfer means, and the transfer means is removed. The removed transfer means is cut and at least partially flattened on a substantially flat molding surface and the partially flattened layer is outlined on the molding surface to so as form a pattern for the cushion layer of the liner.

The transfer means is then discarded and a mold edge or containment wall is used to outline the pattern. This edge defines the desired edge of the cushion layer. In combination with the flattened tape layer, the edge forms a mold for construction of the cushion layer. Once the mold is formed, liquid silicon is poured into it, preferably to a thickness of about ⅛ inch. In preferred embodiments, a parting agent or film is laid over the silicone and the mold is flattened between parallel plates to ensure a uniform thickness. In alternative embodiments, the cushion layer can be formed by any suitable means. For example, a negative corresponding to the inner surface of the socket could be provided. When the positive coated with the inner layer is placed in the negative, the cushioning material could be poured or injected into a clearance between the two. Other techniques for forming the cushion layer will be known to those skilled in the art.

Once the silicone cushion layer 30 has cured, it is removed from the mold. If bead 12 has not already been applied to inner layer 20, bead 12 is affixed in the desired position on inner layer 12. Cushion layer 30 is then shaped and wrapped around the outside of inner layer 20 and glued in place. During this process, the edges of cushion layer 30 are brought up to bead 12 so that a continuous cushion layer is defined. If cushion layer 30 is formed from a pattern that is slightly smaller than the desired surface, it can be slightly stretched as it is affixed to inner layer 20, ensuring a smooth and even fit.

Outer layer 40 is applied to the outer surface of cushion layer 30. In preferred embodiments, outer layer 40 comprises another layer of fiber such as stockinet applied to the outside of cushion layer 30, enclosed in a removable airtight layer, and impregnated with liquid silicone as described above.

When a liner 10 has been constructed in accordance with the present invention, bead 12 will define the finished dimension, shape, contour and texture of the proximal or upper edge of the liner. Because it is designed for this precise purpose, is provides superior comfort over previously known liner technologies.

It is preferred to use urethane or silicone for the construction of all layers of liner 10, in part because those materials can be doped with mineral oil, vitamin E, and/or other additives that improve wearer comfort, and also because those two materials do not lend themselves to use with other adhesives.

While preferred embodiments of this invention have been shown and described, modifications thereof can be made by one skilled in the art without departing from the scope or teaching of this invention. For example, the materials from which the components of the present liner are made may be varied, the shape and configuration of the finished liner may be varied, and the steps used in constructing the liner may be modified. Accordingly, the scope of protection is not limited to the embodiments described herein, but is only limited by the claims that follow, the scope of which shall include all equivalents of the subject matter of the claims. Likewise, the sequential recitation of steps in a claim, unless explicitly so stated, is not intended to require that the steps be performed in any particular order or that a particular step be completed before commencement of another step.

What is claimed is:

1. A liner for use with a prosthesis, comprising:
an inner layer;
a cushion layer affixed to said inner layer;
an outer layer affixed to said cushion layer; and
a bead affixed to at least one of said layers and defining the upper edge of the liner;
wherein the bead is at least partially disposed between said inner layer and said outer layer.

2. A liner for use with a prosthesis, comprising:
an inner layer;
a cushion layer affixed to said inner layer;
an outer layer affixed to said cushion layer; and
a bead affixed to at least one of said layers and defining the upper edge of the liner, wherein the head has a non-uniform thickness.

3. The liner according to claim 2 wherein said inner layer and said outer layer each comprise a fiber impregnated with an elastomer.

4. The liner according to claim 2 wherein said bead comprises urethane or silicone.

5. The liner according to claim 2 wherein the bead is affixed to said outer layer.

6. The liner according to claim 2 wherein the bead is at least partially disposed between said inner layer and said outer layer.

7. A method for making a liner for use between a residual limb and a prosthesis, comprising:
   a) making a positive of the residual limb;
   b) constructing an inner layer on the outer surface of the positive;
   c) defining an upper edge of the liner;
   d) applying a bead along the upper edge of the liner
   e) forming a mold that reflects the shape of the positive and the defined upper edge;
   f) using the mold to shape a cushion layer that has a defined upper edge;
   g) applying the cushion layer to the inner layer; and
   h) constructing an outer layer on the outer surface of the cushion layer.

8. The method according to claim 7 wherein step h) is carried out such that the bead is at least partially disposed between the inner and outer layers of the liner.

9. The method according to claim 7 wherein step h) is carried out such that the bead is at least partially inside the inner layer of the liner.

10. The method according to claim 7 wherein step h) is carried out such that the bead is at least partially outside the outer layer of the liner.

11. The method according to claim 7 wherein said inner layer and said outer layer each comprise a fiber impregnated with an elastomer.

12. The method according to claim 7 wherein said bead comprises urethane or silicone.

13. The method according to claim 7 whetein said inner layer and said outer layer each comprise a fiber impregnated with an elastomer.

14. The method according to claim 7 wherein the bead has a non-uniform thickness.

15. The method according to claim 7 wherein step e) comprises pouring liquid silicone into the mold.

16. A liner for use with a prosthesis, comprising:
   an inner layer;
   a cushion layer affixed to said inner layer;
   an outer layer affixed to said cushion layer;
   a bead engaging said cushion layer and defining the upper edge of the liner; and
   wherein said bead has a non-uniform thickness.

17. A liner for use with a prosthesis, comprising:
   an inner layer;
   a cushion layer affixed to said inner layer;
   an outer layer affixed to said cushion layer;
   a bead engaging said cushion layer and defining the upper edge of the liner; and
   wherein the bead is at least partially disposed between said inner layer and said outer layer.

18. The liner according to claim 17 wherein the bead is affixed to said inner layer.

* * * * *